(12) United States Patent
Pitha

(10) Patent No.: US 6,576,261 B1
(45) Date of Patent: Jun. 10, 2003

(54) POTENTIATION OF INCLUSION COMPLEX FORMATION OF CYCLODEXTRIN DERIVATIVES

(76) Inventor: Josef Pitha, 10997 Mahlon Price Rd., Deal Island, MD (US) 21821

( * ) Notice: Subject to any disclaimer, the term of this patent is extended or adjusted under 35 U.S.C. 154(b) by 0 days.

(21) Appl. No.: 09/634,598

(22) Filed: Aug. 8, 2000

Related U.S. Application Data

(60) Provisional application No. 60/148,294, filed on Aug. 11, 1999.

(51) Int. Cl.[7] ............................................... A61K 9/14
(52) U.S. Cl. ........................ 424/484; 424/488; 514/524
(58) Field of Search ................................ 424/484, 488; 536/403; 514/524

(56) References Cited

U.S. PATENT DOCUMENTS

| | | | | | |
|---|---|---|---|---|---|
| 5,705,528 | A | * | 1/1998 | Kloog | 514/524 |
| 6,043,050 | A | * | 3/2000 | Takeda et al. | 435/58 |
| 6,048,736 | A | * | 4/2000 | Kosak | 436/536 |

\* cited by examiner

*Primary Examiner*—Carlos A. Azpuru
*Assistant Examiner*—Liliana Di Nola-Baron
(74) *Attorney, Agent, or Firm*—Glenna Hendricks

(57) ABSTRACT

A method is disclosed for the potentiation of formation of inclusion complexes of electroneutral and anionic compounds. Included are compositions containing complexes of two different cyclodextrin species. New complexes containing as guest molecules active agents which have been first converted to salts are also disclosed.

9 Claims, No Drawings

POTENTIATION OF INCLUSION COMPLEX FORMATION OF CYCLODEXTRIN DERIVATIVES

CROSS-REFERENCE TO RELATED APPLICATIONS

This application takes priority from provisional patent application 60/148/294 filed Aug. 11, 1999.

FIELD OF THE INVENTION

This invention relates to the solubilization and stabilization of compounds using cyclodextrins.

BACKGROUND OF THE INVENTION

Cyclodextrins are a group of compounds consisting of, or derived from, the three parent cyclodextrins—alpha-, beta- and gamma-cyclodextrins. Cyclodextrins have numerous uses based on their ability to solubilize and complex chemicals.

Alpha-, beta- and gamma-cyclodextrins cyclodextrins are simple oligosaccharides consisting of six, seven or eight glucose residues, respectively, connected to macrocyles by alpha (1 to 4) glycosidic bonds. Each of the glucose residues of a cyclodextrin contains one primary (O6) and two secondary hydroxyls (O2 and O3) which can be substituted, for example, methylated. Many cyclodextrin preparations in practical use are mixtures of chemically individual derivatives in which only a part of hydroxyl groups were substituted and which differ in number and position of these substituents.

This invention uses many different cyclodextrin derivatives including several mixtures of partially methylated cyclodextrins. One composition is a commercial preparation (Wacker Chemie, Beta W7M1.8) in which the methyl substituents are about equally distributed between the primary and secondary hydroxyls of glucose residues; it is abbreviated here as RAMEB. A second class has methyls predominantly substituting for hydrogen at the secondary hydroxyls. These are prepared as described in U.S. Pat. No. 5,681,828 and are referred to as Pitha's methyl derivatives. A third type of methylated cyclodextrins is formed by those cyclodextrin derivatives or their mixtures that have more than half of their secondary hydroxyl groups (i.e., O2 and O3) methylated. For brevity, these are called "highly methylated cyclodextrins." Other mixtures of cyclodextrin derivatives used in this work are partial 2-hydroxypropyl ethers, abbreviated as HPACD, HPBCD or HPGCD for derivatives of alpha-, beta- and gamma-cyclodextrins, respectively.

In addition to the mixtures described in the preceding paragraph, the invention also uses five chemically individual cyclodextrin derivatives: (1) fully methylated alpha-, beta- and gamma-cyclodextrins, abbreviated as TRIMEA, TRIMEB and TRIMEG, respectively, (2) dimethyl derivative of beta-cyclodextrin, DIMEB, in which all glucose residues carry methyl groups on O2 and O6, and (3) maltosyl derivative of beta-cyclodextrin, G2, in which beta-cyclodextrin carries maltosyl residue on O6. The compounds under (1) are of the group of highly methylated cyclodextrins and, like the highly methylated mixtures, have unique properties. Compounds under (2) and (3) do not belong to this group.

Cyclodextrins solubilize insoluble compounds into polar media by forming what is known as an inclusion complex between the cyclodextrin and the insoluble compound; cyclodextrin solubilization power is directly proportional to the stability of the complex. Inclusion complexes are non-covalent associations of molecules in which a molecule of one compound, called the host, has a cavity in which a molecule of another compound, called a guest is included. Derivatives of cyclodextrins are used as the hosts and the insoluble compound is the guest.

Although cyclodextrins and derivatives solubilize many compounds, they are not useful in all cases. For numerous compounds of general interest, cyclodextrins do not have sufficient solubilizing power to make their use practicable. Overcoming this defect requires using large amounts of host compound. However, this is not only uneconomical (making cyclodextrins too expensive for many applications), but also dangerous. Cyclodextrins in very large amounts can boost the effects of various toxicants potentially present outside and in the body itself (Horsky, J. & Pitha, J., J. Incl. Phen. & Mol. Rec. Chem., 18, 291–300, 1994).

Previous art relevant to the current invention discusses three areas of interest: a) highly methylated cyclodextrins, b) doubling cavity size by association of two cyclodextrin moieties and c) forming salts of guest compounds and choosing counterions when forming complexes between cyclodextrin hosts and ionic guests.

Previous art concerning modification of cyclodextrin hosts has been marginally concerned with highly methylated cyclodextrins. The reason for this lack of interest is that the most accessible compound of this group, TRIMEB, was found to be a weak host for several guests (J. Szejtli, Ccylodextrin Technology, Kluwer Academic Publishers, Dordrecht, 1988, p.56). TRIMEA, since it is a derivative of the smallest parent cyclodextrin, was assumed to have a too small cavity. See, for example, A. R. Hedges, Chem. Rev., 98, 2035–2044, 1998; K. Uekama et al., Chem. Rev., 98, 2045–2076, 1998; U.S. Pat. No. 4,687,738; Japanese Patent JP 10319587A; J. Szejtli, Cyclodextrin Technology, Kluwer Academic Publishers, Dordrecht, 1988 and references therein.

Previous art concerning doubling cavity size by using two cyclodextrin moieties relied on connection of these moieties by chemical (covalent) bonds. Specific chemical connection is required for such designs to be effective (K. Fujita et al., J. Chem. Soc. Chem. Commun., 1277–1278, 1984; R. Breslow et al., J. Amer. Chem. Soc., 118, 8495–8496, 1996). Additionally, molecules of some guests are known to form complexes with two molecules of the same cyclodextrin derivative. Such complexes are termed 1:2 complexes and often accompany the usual 1:1 complexes. The present invention shows that some combinations of two different cyclodextrin derivatives lead to better inclusion by host molecules.

Previous art describing complex formation by ionic guests is extensive. A review of those systems, in which parent cyclodextrins were used, counts 271 systems for alpha-cyclodextrin and 342 for beta-cyclodextrin alone (K. A. Connors, J. Pharm. Sci., 84, 843–848, 1995). Statistically, the complexes of anionic guests have about twice the stability compared to corresponding uncharged guests, but there are numerous cases where the situation is reversed and the uncharged guest is preferred. It is not possible to predict whether a specific guest will have greater stability in charged or uncharged state. In previous art, the bases used to form anions of guests were non-volatile and inorganic; many of the guests described there have been used as drugs.

U.S. Pat. No. 4,727,064 discloses that ionization of guest molecules may be an important factor in formation of inclusion complexes of hydroxypropyl derivatives of cyclodextrins and that formation is affected by counterions. Solubilization of retinoic acid in its acidic form and in the form of its sodium, choline and ethanolamine salts were compared and found to increase in that order. The patent also teaches how to prepare such complexes in solid form.

U.S. Pat. No. 5,120,720 and an article by Pitha, Hoshino, Torres-Labandeira and Irie (International Journal of Pharmaceutics, 80, 255–258, 1992) describe a method for preparing inclusion complexes in which a volatile base, ammonia, was used to bring fast dissolution of acidic guests wherein the cyclodextrin derivative was added immediately after the dissolution. The majority of the volatile base was removed with water after solid complexes were prepared.

Related work described later taught addition of bases or organic acids facilitated the solubilization of drugs while cyclodextrins or cyclodextrin derivatives were already present in solutions (E. Fenyvesi et al., The 7th International Cyclodextrins Symposium, Tokyo 1994, Proceedings, pp. 414–418; E. Fenyvesi et al., The 8th International Cyclodextrin Symposium, Budapest 1996, Programme and Abstracts 3-p48; Italian Patent Application M193 A000 141; PCT WO 95/28965; U.S. Pat. No. 5,773,029). The inventors call their system a multiple complex formation by cyclodextrin derivatives. In their claims, they specify that the characteristic of multicomponent inclusion complexes is the simultaneous salt formation and complexation.

SUMMARY OF THE INVENTION

The present invention discloses new methods which have wide applicability to potentiate formation of inclusion complexes between cyclodextrins and guests. These methods were discovered during attempts to solubilize a test compound, S-farnesylthiosalicylic acid (abbreviated as FTS), a potential drug. Highly methylated cyclodextrins were found to form non-covalent complexes with less substituted cyclodextrins spontaneously and rapidly. Such complexes of two cyclodextrin derivatives were found to have a better ability to form an inclusion complex with specific guests than either of the two cyclodextrin derivatives alone. By this procedure, FTS in its acidic form, which is highly water insoluble, was solubilized. Salts of FTS, which have higher water solubility than the acidic form, were well solubilized by these complexes of two cyclodextrin derivatives. However, in this case, even one cyclodextrin derivative leads to useful dissolution. Complexes of two cyclodextrin derivatives, or their components also dissolved representative organics and stabilized colloidal inorganics. In addition to solubilizing water insoluble compounds, complexes of two cyclodextrin derivatives have applications in analytical chemistry for separation of various compounds based on their ability to form inclusion complexes with two cyclodextrins.

DETAILED DESCRIPTION OF THE INVENTION

In order to evaluate systematically the solubilization potency of the available cyclodextrin preparations and of their combinations, test compound, S-farnesylthiosalicylic acid (abbreviated as FTS), was used. This compound is a candidate anticancer drug and, in its acidic form, has very low water solubility. Several combinations of cyclodextrin preparations were found to be better solubilizers of FTS in acidic form than any cyclodextrin preparation alone.

Example 1 shows potentiation of inclusion complex formation using various combinations of two cyclodextrin hosts. The best combinations are those containing highly methylated alpha-cyclodextrin and less methylated, or substituted, beta-cyclodextrin derivatives. The latter may lack any substitutions at the secondary hydroxyls (e.g., G2). The highly methylated alpha-cyclodextrin can be replaced by the corresponding beta- or gamma-derivatives, but the more preferred complex is formed using the former. On the basis of steric considerations, complexes also can be expected to form between highly methylated and less highly methylated alpha-cyclodextrins.

Both the type of cyclodextrin and the kind of substituents are important. The combination of alpha- and beta-cyclodextrin, when used in their hydroxypropylated form, lacks some desirable properties sought. For an improved combination, the inclusion complexes are best formed in a cooperative manner. This cooperativity is measured, in Example 1, by a cooperativity index, which denotes the solubilization of a combination divided by the sum of solubilization components acting separately. Salts of FTS have higher water solubility than FTS in the acidic form and, as shown in Example 1, easily form complexes with cyclodextrin derivatives. Thus, the present invention discloses as preferred inclusion complexes formed by two different cyclodextrin derivatives.

Example 2 shows that the cyclodextrin components of one of the cooperative combinations, TRIMEA-DIMEB, associate spontaneously by themselves; that is, the presence of a guest is not required. Example 3 shows results of evaluation by the continuous variation method indicating that, when combining TRIMEA-DIMEB, about equal amounts of these cyclodextrin components are required for optimal solubilization. Since their molecular weights are similar (1225 and 1331 respectively), this shows that the inclusion complex involves one molecule of TRIMEA and one of DIMEB. [It may be noted that a process similar to formation of inclusion complexes is used in all known living systems for repair of proteins that are in non-native conformation. One of these systems consists of a large subunit chaperonin, GroEL, which has a seven sided cavity that is capped, as by a lid, by co-chaperonin GroES (M. Shtilerman et al., Science, 284, 822–825, 1999).] The TRIMEA-DIMEB combination of this invention has a formal similarity to this chaperonin system. Further, the data in Example 3 shows that the relation between solubilization and concentration of cyclodextrin hosts is about linear. In other words, solutions of the guest in this particular combination of cyclodextrin derivatives will not precipitate the guest upon dilution with water or aqueous solvent. This is an important property for applications in pharmaceuticals and cleaning compositions. Results in Example 4 show that complexes resulting from combinations of cyclodextrins work effectively for solubilization of several water insoluble compounds in addition to FTS.

Complexes of combinations of cyclodextrins also have applications in analytical separations of compounds. Since cyclodextrins are optically active, these complexes can be used for the separation of optically isomeric compounds. A suitable system is shown in Example 5. In this system, TRIMEA-like molecules are immobilized on a solid support which is then used in a column. A mixture of guests to be separated is introduced into the column in a solution containing DIMEB-like molecules and is subsequently eluted by a similar solution. During the elution, complexes consisting of guests, DIMEB and immobilized TRIMEA form reversibly and guests are separated on basis of their ability to support formation of such complexes. The guest forming the most stable complex is eluted from the column last. Results shown later in Example 7 suggest that columns with immobilized TRIMEA also are effective for separation of proteins. In all instances of complex formation using the present invention, highly methylated alpha-cyclodextrins strongly outperformed highly methylated beta- and gamma-cyclodextrins. The use of alpha-cyclodextrins in analytical applications utilizing immobilized forms of these compounds is deemed of much value.

The highly methylated cyclodextrin component of the above complexes was, for some guest compounds, a useful solubilizing agent on its own. This is documented in the Example 6. Data shows that, for several difficult to dissolve guests, such as retinoic acid or hydrocortisone, TRIMEA outperformed other cyclodextrin hosts. This result may be explained on the basis of the recently published crystal structure of TRIMEA (T. Steiner et al., Angew. Chem. Int. Ed., 37, 3404–3407, 1998). Substitution of all secondary hydroxyls by methyls obviously leads to steric crowding which, in the case of alpha-cyclodextrin, resulted in widening the opening of the cavity on the secondary hydroxyl side and making the cavity more flat. The data in Example 6 show that this structural change makes TRIMEA a very good host on its own. Data of Example 1 shows that the same flat structure also is beneficial for formation of complexes with two cyclodextrin hosts. In these instances, the flat molecule of TRIMEA may function as a lid closing the cavity of the other cyclodextrin host. On basis of these considerations, the structural criterion for compounds of optimal activity can be defined—the majority of the secondary hydroxyls in these compounds must be methylated. The crowding of methyl groups starts when more than half of the secondary hydroxyls are methylated. Hence, this criterion defines compounds expected to be effective—highly methylated cyclodextrins.

In Example 7, it is shown that highly methylated cyclodextrins are effective solubilizers of compounds that, because they are true macromolecules, can not be fully included. Example 8 shows that highly methylated cyclodextrins are more effective hosts than otherwise substituted cyclodextrins in formation and stabilization of inorganic guests. Colloidal particles of an electricity-conducting metal, copper, were made and stabilized; the same procedure also was used for preparing a colloidal composition of a ferromagnetic metal, cobalt. In Example 8, it also is shown that these stabilized colloidal metals are highly reactive and, thus, can be converted by chemical reaction into other colloidal compounds. Example 8, additionally, describes complexes of sulphur with highly methylated cyclodextrins; the resulting complexed sulphur has potential application in electrical batteries. Colloidal compositions of calcium fluoride, which have applications in dentistry, can be made in similar manner.

Example 9 describes preparation and subsequent solubilization of salts of FTS. The choline salt of FTS was extracted from an aqueous medium into chloroform providing a lipophilic product. The aqueous solutions of the cyclodextrin-solubilized choline salt of FTS are neutral and can be used in preparations for parenteral or sublingual administration. Ethanolamine and triethanolamine have a similar biocompactibility and structure to choline and is expected to perform similarly in the process described. The sodium salt of FTS, which was used as an intermediate in the above preparation of choline salt, also forms inclusion complexes and can be used to make pharmaceutical formulations of FTS as well. Nevertheless, all choline salts tested in Example 9 formed cyclodextrin inclusion complexes more efficiently than the corresponding sodium salts.

EXAMPLE 1

Solubilization of FTS by Two Different Hosts

A slight excess of FTS was equilibrated with water containing one host at 5% concentration or two hosts, each at 5% concentration, by rotation for a week. The suspension was then filtered through a millipore filter and the concentration of FTS in filtrate determined by ultraviolet spectrophotometry. Table for Example 1 shows the solubility (mg/ml) obtained with various combinations of two hosts. The cooperativity index reflects the improvement in solubility obtained with each combination of two hosts over the solubility obtained with each of the individual hosts involved in the two-host system. It is computed by dividing the obtained solubility with two hosts by the sum of the individual solubilities obtained with each component. Thus, a cooperativity of 9.4 means that the solubility with two hosts is much higher than that for each component and use of two hosts greatly improves solubility of the guest; a solubility of 1.0 means there is Table for Example 1
Enhancement of Solubility of FTS Guest with Various
Combinations of Two Different Hosts

| Host Combinations | Solubility (mg/ml) | Cooperativity (observed ÷ Σ components) |
|---|---|---|
| Alpha-Beta Combination | | |
| Alpha Cyclodextrin - DIMEB | 1.4 | 1.0 |
| Alpha Cyclodextrin - TRIMEB | 0.1 | 0.6 |
| Pitha Methyl 322 - DIMEB | 1.3 | 0.7 |
| TRIMEA - G2 | 3.9 | 3.0 |
| TRIMEA - Pitha Methyl 258 | 5.7 | 9.4 |
| TRIMEA - DIMEB | 6.6 | 4.1 |
| HPACD - HPBCD | 0.052 | 0.3 |
| Beta - Beta Combination | | |
| Beta Cyclodextrin - TRIMEB | 0.026 | 0.2 |
| G2 - DIMEB | 2.4 | 1.0 |
| G2 - TRIMEB | 1.1 | 1.0 |
| Pitha Methyl 258 - TRIMEB | 0.95 | 1.4 |
| DIMEB - TRIMEB | 2.6 | 1.8 |
| DIMEB - PERM HPBCD | 1.1 | 0.8 |
| Beta - Gamma Combination | | |
| G2 - TRIMEG | 1.0 | 1.0 |
| DIMEB - TRIMEG | 1.4 | 1.0 |

*Perm HPBCD is HPBCD in which all hydroxyl groups are methylated. All other compounds are described in the 'Background of the Invention' section no enhancement with two hosts. Water was used as the solvent for all data in the Table for Example 1. When a sodium carbonate based buffer of pH 10 was used as a solvent (conditions in which FTS is converted to its salt), the solubility of FTS in TRIMEA combined with DIMEB or in TRIMEA combined with Pitha methyl derivatives exceeds 60 mg per ml. Cooperativity, in this case, could not be calculated since, in these conditions, even solubilization by one component alone (DIMEB or Pitha methyl derivative) was over 60 mg per ml.

EXAMPLE 2

Formation of Complex with Two Different Hosts in Absence of a Guest

TRIMEA and DIMEB dissolve in water more than 33 g per 100 ml of water. The solubilities of both these compounds in water can be decreased by the addition of salts or by an increase of temperature. Thus, in aqueous solution of sodium sulfate (1 M), TRIMEA dissolved to the saturation concentration just of 0.4 mg/ml and DIMEB to 3.4 mg/ml. When both TRIMEA and DIMEB were present, the amount of total carbohydrate dissolved was found to be 1.55 mg/ml higher than the sum of the individual saturation concentrations. If a 1:1 complex between TRIMEA and DIMEB is assumed to form, the association constant of 700 [1/M] can be estimated for that complex, which is of the same order of magnitude as association constants of many complexes formed of guests and cyclodextrins.

EXAMPLE 3

Characterization of Solubilization of FTS by Two Different Hosts

The optimum ratio of hosts was established by the continuous variation method, using techniques of Example 1 and water as a solvent. The results in Table A for Example 3 indicate that the optimum solubility is obtained when both hosts are in about equal concentrations.

Concentration dependence of solubilization of FTS by two hosts shows the dependence is close to linear, as shown in Table B for Example 3. The pharmaceutical formulations based on such solutions will not precipitate upon dilution and are suitable for parenteral, intranasal and ophthalmic applications.

Table A for Example 3
Effects of Each Most on Solubilizing the FTS Guest

| TRIMEA (% w/w) | DIMEB (% w/w) | FTS (mg/ml) |
|---|---|---|
| 5 | 0 | 0.19 |
| 4 | 1 | 2.33 |
| 3 | 2 | 2.79 |
| 2 | 3 | 2.66 |
| 1 | 4 | 2.29 |
| 0 | 5 | 1.55 |

Table B for Example 3
Concentration Dependence in Systems of Two Different Hosts

| TRIMEA (% w/w) | DIMEB (% w/w) | FTS (mg/ml) |
|---|---|---|
| 2 | 2 | 2.13 |
| 5 | 5 | 8.53 |
| 10 | 10 | 15.86 |
| 15 | 15 | (>than 17.17, all dissolved) |

EXAMPLE 4

Solubilization of Additional Guests by Two Different Hosts

Techniques were as described in Example 1 and water was used as a solvent. As shown in Table for Example 4, complexes of two hosts increased the solubility of retinoic acid and taxol compared to the solubility obtained with individual hosts.

Table for Example 4
Solubilization of Additional Guests by Two Different Hosts

| Guest | Host Combination | Solubility (mg/ml) | Cooperativity (observed + Σ components) |
|---|---|---|---|
| Amphotericin B | TRIMEA - DIMEB | 0.185 | 0.9 |
|  | DIMEB - TRIMEB | 0.131 | 0.7 |
|  | DIMEB - TRIMEB | 0.158 | 0.9 |
| Retinoic Acid | TRIMEA - DIMEB | 0.071 | 1.45 |
|  | TRIMEA - Pitha Methyl 258 | 0.052 | 1.13 |
|  | TRIMEA - RAMEB | 0.056 | 1.08 |
|  | TRIMEA - TRIMEB | 0.012 | 0.7 |
| Taxol | TRIMEA - DIMEB | 1.00 | 1.49 |

EXAMPLE 5

Use of Complexes of Two Hosts in the Analytical Separation of Compounds

A column with immobilized, highly methylated cyclodextrin is prepared in a three-step procedure. In the first step, a cyclodextrin derivative, which is methylated on all hydroxyls except for few of the primary hydroxyls, was made by a process described by N. Lupescu et al. (J. Carbohydrate Chem. 18, 99–104, 1999). In this process, the cyclodextrin is treated in a strongly alkaline medium, first with a bulky sililation agent (e.g., tertiary-butyldiphenylsilyl chloride), then with an excess of methylation agent (e.g., methyl iodide) and, after an appropriate interval, with a desililation agent (e. g. ammonium fluoride). In the second step, the above derivative is alkylated by allyl chloride or another reagent, which introduces a substituent terminated by a double bond. In the third step, the above derivative is immobilized on column material containing free SH groups by Kharash addition, a reaction catalyzed by free radicals. Such addition was used successfully in the past in preparation of carbohydrate based affinity columns (M. G. Caron et al., J. Biol. Chem., 254, 2923–2927, 1979). For preparation of silicagel or silica based column materials, the appropriate starting material is treated with SH terminated sililation reagents, which are commercially available (Y. Prigent et al., 10th Internat. Symp. on Chiral Discrimination, Vienna 1998, cmp. abstract Cyclodextrin News 13, 127, 1999). Alternatively, the immobilization of cyclodextrin host on a solid support can be performed by methods developed by Armstrong et al. for immobilization of heptakis-2, 3-O-dimethyl-beta-cyclodextrin (D. W. Armstrong et al., J. Lig. Chrom. & Rel. Technol., 20, 3279–3308, 1997). The sample to be separated on columns containing immobilized highly methylated cyclodextrins is introduced in aqueous solution containing the other component of the two cyclodextrin derivative complex, for example, DIMEB or RAMEB and optional salt. Elution is performed using a gradient in which cyclodextrin component or salt or both are gradually decreased by methods common in the art.

EXAMPLE 6

Solubilization by a Single, Highly Methylated Host

The same techniques as in Example 1 were used, with water as the solvent. Table for Example 6 shows the solubility obtained with various guests and highly methylated hosts. The last host compound used for each guest compound (denoted by *) is that which is currently considered an effective solubilizer. The single, highly methylated cyclodextrin host outperformed the current standard for FTS (over 2 times), hydrocortisone (1.3 times), and retinoic acid (2.5 times).

Table for Example 6
Solubilization of Various Guests by a Highly Methylated Host

| Guest | Host (5% in water) | Solubility (mg/ml) |
|---|---|---|
| Amphotericin B | TRIMEA | 0.093 |
|  | TRIMEB | 0.065 |
|  | TRIMEG | 0.068 |
|  | HPGCD* | 0.15 |
| FTS | TRIMEA | 0.19 |
|  | TRIMEB | 0.12 |
|  | TRIMEG | 0.045 |
|  | HPBCD* | 0.091 |
| Hydrocortisone | TRIMEA | 6.4 |
|  | TRIMEB | 2.1 |
|  | TRIMEG | 1.1 |
|  | HPBCD* | 5.0 |
| Retinoic Acid | TRIMEA | 0.10 |
|  | TRIMEB | 0.007 |
|  | DIMEB* | 0.04 |
| Taxol | TRIMEA | 0.29 |
|  | DIMEB* | 0.38 |

EXAMPLE 7

Stabilization and Solubilization of a Protein by Highly Methylated Cyclodextrins The protein, insulin, was dissolved in 30% acetic acid, conditions in which it is known to be present as a monomeric specie. This insulin solution was subsequently introduced into a phosphate buffered solution containing the cyclodextrins at 2 or 4% concentrations; the final concentration of insulin was 1 mg/ml and final pH was less than 6. In these conditions, a part of insulin aggregated and precipitated from the solution. The highly methylated cyclodextrin, TRIMEA, was a more effective stabilizer of the dissolved insulin than DIMEB or TRIMEB. No cooperative effects were found. This was to be expected because monomeric insulin has a molecular weight at least three times higher than that possibly accommodated by a combined cavity.

EXAMPLE 8

Inorganic Guests—Formation and Stabilization

Aqueous ammonia was added to a solution of cupric sulfate pentahydrate (0.1 g) in water (50 ml) until a precipitate formed. The precipitate was then dissolved again to form a deep blue solution. To 2 ml samples of this solution, cyclodextrin derivatives were added to a final 5% concentration. After the dissolution, the samples were cooled in an ice bath and hydrazine hydrate (10 microliters) was added; the samples turned colorless. Then, the samples were placed for 25 minutes into an ultrasound bath partially filled with ice. At this point, the brown color of colloidal copper appeared and was quantified by measurement of absorbance at 420 nm; results are shown in Table for Example 8. Properly dispersed colloidal copper, when compared to the aggregated copper is much more highly reactive and can be easily converted into copper compounds. To prove that the dispersed, colloidal copper made by this method was protected from aggregation by cyclodextrin derivatives, the samples were left at room temperature and exposed to air, so that oxygen would covert colloidal copper, which is in active form, to cupric oxide, which dissolves in ammonia to give blue cupric ions. The final concentration of soluble cupric ions was quantified by measurement of absorbance at 570 nm. From these results, the percentages of copper in active form were calculated and are shown in Table for Example 8. The results show that cyclodextrin derivatives promote the formation of very reactive colloidal copper and subsequently protect it from aggregation. Similar results were obtained using cobalt salts, but a longer sonication period had to be used. Complexes of sulphur and highly methylated cyclodextrin are prepared by equilibration in aqueous media or are isolated from melts of elementary sulphur with cyclodextrins in which all hydroxyl groups were converted to methyl ether groups. Methylated cyclodextrins (DIMEB and Pitha methyl derivative) alone or in combination with TRIMEA were effective in preparation (by precipitation from solutions of calcium chloride and sodium fluoride) and stabilization of colloidal compositions of calcium fluoride, a compound of possible use in remineralization of dental enamel. The metallic inclusion complexes produced in accord with the methods of the invention may be used in electronic devices.

Table for Example 8
Formation and Stabilization of Colloidal Copper by Cyclodextrin Derivatives

| Addition | Absorbance at 420 nm | Copper in Active Form (%) |
|---|---|---|
| None | .102 | 6% |
| G2 | .437 | less than 100%* |
| TRIMEA | .520 | 100% |
| DIMEB | .110 | 100% |
| TRIMEA & DIMEB | .508 | 100% |

*Could not be quantified due to slow decomposition of G2 during the experiment.

EXAMPLE 9

Preparation and Solubilization of Salts of FTS and Advantageous Properties of Choline Salts of Other Anions Aqueous sodium carbonate (5%, 10 ml) was added to the stirred suspension of FTS (80 mg) in water (5 ml) containing choline chloride (304 mg). Chloroform (20 ml) was then added to extract the choline salt of FTS: the resulting emulsion was stirred for about an hour. The chloroform extract had to be separated by centrifugation (10 min, 3000 rpm) and was then dried overnight with anhydrous magnesium sulfate. Evaporation of the dried and filtered chloroform extract yielded a colorless, glassy residue (93 mg), to which was added a solution of methylated beta-cyclodextrin (1.2 g) in water (10 ml). After overnight stirring, the dissolution of the glassy, choline salt of FTS residue was about complete and the solution was filtered through a millipore filter and evaporated in vacuo. The solid obtained thereby was heated on a boiling water bath. Upon heating, the residue formed a solid foam (1.18 g) that could be ground to a white powder. A sample of this powder dissolved easily and fully in water giving a solution of pH 6.5 (paper strip indicator), which had an absorbance of 111 units at 260 nm. From these data, the concentration of FTS in the powder was calculated to be 3.5% w/w.

Choline salts of FTS are not the only ones that can be solubilized by cyclodextrin derivatives. A sodium salt formed by sodium carbonate as described above, or made by the procedure that follows, can be used as well. In this procedure, FTS (10 mg, 28 micromoles) was dissolved with warming in ethanol (20 microliters) and an aqueous solution of sodium hydroxide (30 microliters of 1 M NaOH carbonate free, i.e., 30 micromoles) was added. The precipitate that formed upon the addition dissolved promptly upon stirring. This clear solution then was added to the solution of Pitha methyl derivative (100 mg) in isotonic phosphate buffered saline (1 ml, pH 7.4). The pH of the resulting solution was adjusted to the original value, taking care that acidification did not precipitate FTS in its acidic form. The resulting solution remained clear for an extended period of time and is suitable for injection. It also can be freeze or spray dried to form powders, which also dissolve in water clearly. If such solutions are acidified, precipitate forms slowly. Solubilized choline salts of FTS are less prone to form precipitate upon acidification than sodium salts. However, with proper care, sodium salts of FTS can be used safely.

Choline salts, nevertheless, had an advantage over sodium salts in all cases investigated. In these investigations, choline salts were prepared by extraction with organic solvents of mixtures of sodium salts of the anion in question and choline chloride. There mixtures were either solid or in aqueous solutions. Choline salts obtained by evaporation of organic solvents were easily solubilized by aqueous solutions of methylated beta-cyclodextrin or by the parent gamma-cyclodextrin. The representative drugs tested were of the following acid types: (1) carboxylic acids (the previously described FTS, salicylic acid, ibuprofen, indomethacin, ampicillin, amphotericin B); (2) acids of the phenolic type (piroxicam); (3) sulfates and sulfonates (dehydroepiandrosterone sulfate, suramin); and (3) compounds with an acidic nitrogen atom (sulfadiazine). The variety of acid types which were tested successfully shows that a similar advantage can be expected when other mildly acidic compounds are converted to choline, ethanolamine or triethanolamine salts followed by solubilization in methylated beta-cyclodextrin and parent gamma-cyclodextrin.

What is claimed is:

1. A composition of matter comprising a methylated beta-cyclodextrin or parent gamma-cyclodextrin, said cyclodextrin having as a guest molecule a biologically active agent in the form of a choline, ethanolamine or triethanolamine salt.

2. The composition of claim 1 wherein said active agent is an anti-cancer agent.

3. The composition of claim 2 wherein said anti-cancer agent is S-farnesylthiosalicylic acid.

4. A method of preparing a pharmaceutical formulation of the medicinal S-farnesylthiosalicylic acid comprising the steps of:

(1) preparing a salt of said medicinal, then
(2) dissolving the salt formed in step 1 in an aqueous solution of cyclodextrins and allowing formation of inclusion complexes containing said medicinal as a guest molecule and adjusting pH to provide a pharmaceutically acceptable composition.

5. The method of claim 4 wherein the product of step 2 is subjected to a dehydrating process.

6. A composition of matter comprising at least one salt of S-farnesylthiosalicylic acid chosen from S-farnesylthiosalicylic acid choline salt, S-farnesylthiosalicylic acid ethanolamine salt, or S-farnesylthiosalicylic acid triethanolamine salt in a pharmaceutically acceptable carrier.

7. The composition of claim 6 wherein the salt is present as a guest molecule in at least one cyclodextrin.

8. A method of preparing an anti-cancer agent for administration comprising complexing with cyclodextrin compositions comprising, in combination, a first cyclodextrin wherein >50% of the secondary hydroxyl groups of the parent cyclodextrin have been converted to methoxy groups, a second cyclodextrin wherein ≦50% of the secondary hydroxyl groups of the parent cyclodextrin have been converted to methoxy groups, and an anti-cancer agent which is sparingly soluble or insoluble in water wherein the combination said first and second cyclodextrins results in cooperativity index of >1.

9. The method of claim 8 wherein the anti-cancer agent is a salt of S- Farnesylthiosalicylic acid.

* * * * *